(12) United States Patent
Scirica et al.

(10) Patent No.: US 11,357,507 B2
(45) Date of Patent: Jun. 14, 2022

(54) SURGICAL STAPLING DEVICE FOR PERFORMING CIRCULAR ANASTOMOSIS AND SURGICAL STAPLES FOR USE THEREWITH

(71) Applicant: Covidien LP, Mansfield, MA (US)

(72) Inventors: Paul Scirica, Huntington, CT (US); David Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 230 days.

(21) Appl. No.: 16/665,272

(22) Filed: Oct. 28, 2019

(65) Prior Publication Data

US 2020/0054339 A1 Feb. 20, 2020

Related U.S. Application Data

(63) Continuation of application No. 15/689,707, filed on Aug. 29, 2017, now Pat. No. 10,537,331, which is a
(Continued)

(51) Int. Cl.
*A61B 17/068* (2006.01)
*A61B 17/115* (2006.01)
(Continued)

(52) U.S. Cl.
CPC ...... *A61B 17/1155* (2013.01); *A61B 17/0644* (2013.01); *A61B 2017/07235* (2013.01); *A61B 2017/07264* (2013.01)

(58) Field of Classification Search
CPC ..... A61B 17/11; A61B 17/064; A61B 17/068; A61B 17/115; A61B 17/0644;
(Continued)

(56) References Cited

U.S. PATENT DOCUMENTS

| 4,289,133 | A | 9/1981 | Rothfuss |
| 4,319,576 | A | 3/1982 | Rothfuss |

(Continued)

FOREIGN PATENT DOCUMENTS

| EP | 2110085 A2 | 10/2009 |
| EP | 2436318 B1 | 11/2016 |

(Continued)

OTHER PUBLICATIONS

Chinese Office Action (with English translation), dated Jan. 5, 2016, corresponding to Chinese Application No. 201110274263.8; 18 total pages.

(Continued)

*Primary Examiner* — Eyamindae C Jallow

(57) ABSTRACT

An anvil assembly, an end effector, and/or a surgical stapler are suitable for performing curved or circular anastomosis and/or treatment to internal walls of hollow tissue organs. The anvil assembly includes an anvil center rod and an anvil head secured to a distal end of the anvil center rod. The anvil head includes an anvil plate defining a tissue contact surface and a plurality of staple forming pockets formed in the tissue contact surface of the anvil plate. Each of the staple forming pockets defines an arcuate longitudinal axis.

20 Claims, 10 Drawing Sheets

Related U.S. Application Data continuation of application No. 13/207,653, filed on Aug. 11, 2011, now Pat. No. 9,750,502.

(60) Provisional application No. 61/410,980, filed on Nov. 8, 2010, provisional application No. 61/388,788, filed on Oct. 1, 2010.

(51) Int. Cl.
*A61B 17/064* (2006.01)
*A61B 17/072* (2006.01)

(58) Field of Classification Search
CPC ............ A61B 17/1144; A61B 17/1155; A61B 2017/07235; A61B 2017/07242
USPC ......... 227/175.1, 175.2, 175.3, 175.4, 176.1; 606/1, 53, 60, 75, 213–219, 232, 300
See application file for complete search history.

(56) References Cited

U.S. PATENT DOCUMENTS

| | | | |
|---|---|---|---|
| 5,389,098 A | 2/1995 | Tsuruta et al. | |
| 5,497,933 A | 3/1996 | DeFonzo et al. | |
| 5,560,532 A | 10/1996 | DeFonzo et al. | |
| 5,816,471 A | 10/1998 | Ley et al. | |
| 5,817,109 A | 10/1998 | McGarry et al. | |
| 5,839,639 A | 11/1998 | Sauer et al. | |
| 5,915,616 A | 6/1999 | Viola et al. | |
| 7,080,769 B2 | 7/2006 | Vresh et al. | |
| 7,234,624 B2 | 6/2007 | Gresham et al. | |
| 7,325,713 B2 | 2/2008 | Aranyi | |
| 7,398,907 B2 | 7/2008 | Racenet et al. | |
| 7,398,908 B2 | 7/2008 | Holsten et al. | |
| 7,407,075 B2 | 8/2008 | Holsten et al. | |
| 7,455,682 B2 | 11/2008 | Viola | |
| 7,611,038 B2 | 11/2009 | Racenet et al. | |
| 7,744,627 B2 | 6/2010 | Orban, III et al. | |
| 7,922,743 B2 | 4/2011 | Heinrich et al. | |
| 8,066,169 B2 | 11/2011 | Viola | |
| 8,113,406 B2 | 2/2012 | Holsten et al. | |
| 8,123,103 B2 | 2/2012 | Milliman | |
| 8,181,838 B2* | 5/2012 | Milliman .................. | A61B 1/31 227/175.1 |
| 8,231,042 B2 | 7/2012 | Hessler et al. | |
| 8,328,063 B2 | 12/2012 | Milliman et al. | |
| 8,453,910 B2 | 6/2013 | Bettuchi et al. | |
| 8,453,911 B2 | 6/2013 | Milliman et al. | |
| 8,464,924 B2 | 6/2013 | Gresham et al. | |
| 8,511,533 B2 | 8/2013 | Viola et al. | |
| 8,540,132 B2 | 9/2013 | Marczyk et al. | |
| 8,806,973 B2 | 8/2014 | Ross et al. | |
| 8,998,061 B2 | 4/2015 | Williams et al. | |
| 9,750,502 B2 | 9/2017 | Scirica et al. | |
| 10,537,331 B2 | 1/2020 | Scirica et al. | |
| 2002/0185517 A1 | 12/2002 | Vresh et al. | |
| 2005/0067454 A1 | 3/2005 | Vresh et al. | |
| 2005/0245965 A1 | 11/2005 | Orban, III et al. | |
| 2007/0027473 A1 | 2/2007 | Vresh et al. | |
| 2007/0034666 A1 | 2/2007 | Holsten et al. | |
| 2007/0034667 A1 | 2/2007 | Holsten et al. | |
| 2007/0034668 A1 | 2/2007 | Holsten et al. | |
| 2007/0057014 A1 | 3/2007 | Whitman et al. | |
| 2007/0181632 A1 | 8/2007 | Milliman | |
| 2007/0194079 A1 | 8/2007 | Hueil et al. | |
| 2008/0041918 A1 | 2/2008 | Holsten et al. | |
| 2009/0001121 A1 | 1/2009 | Hess et al. | |
| 2009/0026245 A1 | 1/2009 | Holsten et al. | |
| 2009/0255976 A1 | 10/2009 | Marczyk et al. | |
| 2009/0255978 A1 | 10/2009 | Viola et al. | |
| 2009/0281554 A1 | 11/2009 | Viola | |
| 2009/0321496 A1 | 12/2009 | Holsten et al. | |
| 2010/0065607 A1 | 3/2010 | Orban, III et al. | |
| 2010/0127039 A1* | 5/2010 | Hessler ................. | A61B 17/115 227/175.1 |
| 2010/0301098 A1 | 12/2010 | Kostrzewski | |
| 2011/0006100 A1 | 1/2011 | Milliam | |
| 2011/0042442 A1 | 2/2011 | Viola et al. | |
| 2011/0057016 A1 | 3/2011 | Bettuchi | |
| 2011/0089219 A1 | 4/2011 | Hessler | |
| 2011/0114701 A1 | 5/2011 | Hessler | |
| 2011/0130788 A1 | 6/2011 | Orban, III et al. | |
| 2012/0012641 A1 | 1/2012 | Milliman et al. | |
| 2012/0080483 A1 | 4/2012 | Riestenberg et al. | |
| 2012/0080492 A1 | 4/2012 | Scirica et al. | |
| 2012/0145768 A1 | 6/2012 | Sorrentino et al. | |
| 2012/0193398 A1* | 8/2012 | Williams ............. | A61B 17/105 227/179.1 |
| 2012/0228356 A1 | 9/2012 | Milliman et al. | |
| 2013/0193192 A1 | 8/2013 | Casasanta, Jr. et al. | |
| 2015/0157323 A1 | 6/2015 | Williams et al. | |

FOREIGN PATENT DOCUMENTS

| | | |
|---|---|---|
| JP | 58018510 | 7/1956 |
| JP | 345096 | 6/1959 |
| JP | 2008512173 A | 4/2008 |
| JP | 2008114072 A | 5/2008 |
| JP | 2010179104 A | 8/2010 |
| JP | 0006030945 B2 | 11/2016 |
| WO | 03094747 A1 | 11/2003 |
| WO | 2006/028314 A1 | 3/2006 |

OTHER PUBLICATIONS

English translation of Chinese Office Action, dated Mar. 2, 2016, corresponding to Chinese Application No. 201310121403.7; 11 pages.

European Communication dated May 31, 2016, corresponding to European Application No. 13162779.6; 6 pages.

Chinese Second Office Action (With English Translation), dated Nov. 1, 2016, corresponding to Chinese Patent Application No. 201310121403 7; 8 total pages.

Japanese Office Action (with English translation), dated Nov. 21, 2016, corresponding to Japanese Application No. 2013-076726; 8 total pages.

Japanese Office Action (with English Translation), dated Apr. 14, 2015, corresponding to Japanese Patent Application No. 2011-195041; 9 total pages.

European Communication dated May 11, 2015, corresponding to European Patent Application No. 13162779.6; 7 pages.

Chinese Office Action (With English Translation), dated Jul. 3, 2015, corresponding to Chinese Patent Application No. 201110274263. 8; 15 total pages.

Japanese Notice of Final Rejection (with English Translation), dated Dec. 15, 2015, corresponding to Japanese Application No. 2011-195041, 7 total pages.

English translation of a microfilm of Japanese Utility Model Application No. 56-113942 (Japanese Laid-Open Utility Model Publication No. 58-018510), dated Jul. 31, 1981, corresponding to Japanese Application No. 2011-195041; 20 pages.

English translation of Japanese Publication for Opposition No. 34/5096, published Jun. 18, 1959, corresponding to Japanese Application No. 2011-195041, 6 pages.

Extended European Search Report corresponding to EP 11 25 0769.4, completed Jul. 23, 2013, and dated Jul. 30, 2013; (6 pp).

Extended European Search Report corresponding to EP 13 16 2779.6, completed Jun. 26, 2013, and dated Jul. 4, 2013; (9 pp).

U.S. Appl. No. 13/156,645, filed Jun. 9, 2011.

Chinese Office Action (With English Translation), dated Jun. 3, 2015, corresponding to Chinese Patent Application No. 201110274263. 8; 15 total pages.

Japanese Office Action with English Summary FOrm, dated Oct. 12, 2017, corresponding to Japanese Application No. 2017-26674; (2 pages).

English translation of Japanese Office Action dated May 27, 2020, corresponding to counterpart Japanese Application No. 2019-003310; 5 pages.

(56) References Cited

OTHER PUBLICATIONS

Japanese Office Action dated Feb. 9, 2022, issued in corresponding JP Appln. No. 2020136236, 5 pages.
European Office Action dated Apr. 5, 2022, issued in corresponding EP Appln. No. 16201936, 7 pages.

* cited by examiner

SURGICAL STAPLING DEVICE FOR PERFORMING CIRCULAR ANASTOMOSIS AND SURGICAL STAPLES FOR USE THEREWITH

CROSS-REFERENCE TO RELATED APPLICATIONS

The present application is a continuation of U.S. patent application Ser. No. 15/689,707, filed Aug. 29, 2017, which is a continuation of U.S. patent application Ser. No. 13/207,653, filed Aug. 11, 2011, now U.S. Pat. No. 9,750,502, which claims the benefit of and priority to each of U.S. Provisional Patent Application Ser. No. 61/410,980, filed on Nov. 8, 2010; and U.S. Provisional Patent Application Ser. No. 61/388,788, filed on Oct. 1, 2010, the entire contents of each of which being incorporated herein by reference.

BACKGROUND

Technical Field

The present disclosure relates generally to a surgical stapling device for applying surgical staples to body tissue. More particularly, the present disclosure relates to a surgical stapling device suitable for performing curved or circular anastomosis and/or treatment to internal tissue and/or to internal walls of hollow tissue organs.

Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. The staples are driven from the staple holding component by a pusher or pushers. An annular knife is concurrently advanced to core tissue with the hollow organ to free a tubular passage within the organ.

Besides anastomosis of hollow organs, surgical stapling devices for performing circular anastomosis have been used to treat internal hemorrhoids in the rectum. Typically, during use of a circular stapling device for hemorrhoid treatment, the anvil head and the staple holding component of the surgical stapling device are inserted through the anus and into the rectum with the anvil head and the staple holding component in an open or unapproximated position. Thereafter, a purse-string suture is used to pull the internal hemorrhoidali tissue towards the anvil rod. Next, the anvil head and the staple holding component are approximated to clamp the hemorrhoid tissue between the anvil head and the staple holding component. The stapling device is fired to remove the hemorrhoidal tissue and staple the cut tissue. A surgical stapler for treating hemorrhoids is disclosed in Heinrich, U.S. Pat. No. 6,959,851, the disclosure of which is hereby incorporated by reference herein.

In circular stapling devices, typically a gap or spacing between adjacent staple forming pockets and corresponding staple retaining pockets, in each annular row, is greater for a radially outward row as compared to a radially inward row. The staples have a straight backspan and the staple forming pockets and staple retaining pockets have a straight longitudinal axis. The inner annular row of staple forming pockets and/or staple retaining pockets determines the number of staples for each annular row. Each annular row has the same or equal number of staple forming pockets and/or staple retaining pockets. Accordingly, the gap between adjacent staple forming pockets and/or staple retaining pockets, in each annular row is greatest in the outer annular row as compared to the inner annular row.

Accordingly, a need exists for providing a circular surgical stapling device wherein the gap between adjacent staple forming pockets and/or staple retaining pockets, in each annular row is reduced or maintained in each annular row thereof, from the outer annular row to internal tissue and/or to the inner annular row.

SUMMARY

The present disclosure relates to an anvil assembly, an end effector and/or a surgical stapler suitable for performing curved or circular anastomosis and/or treatment to internal walls of hollow tissue organs.

According to an aspect of the present disclosure, an anvil assembly for a surgical stapling apparatus is provided. The anvil assembly includes an anvil center rod having a proximal end and a distal end, the center rod defining a central longitudinal axis; and an anvil head secured to the distal end of the anvil center rod. The anvil head includes an anvil plate defining a tissue contact surface; and a plurality of staple forming pockets formed in the tissue contact surface of the anvil plate, wherein each of the plurality of staple pockets has a curved length.

The anvil assembly can have staple forming pockets wherein each staple forming pocket has a radius of curvature extending from the central longitudinal axis of the center rod.

The anvil head may be circular, the anvil plate defining a plurality of annular rows of staple forming pockets. Each annular row of staple forming pockets can include an equal number of staple forming pockets.

A distance between adjacent staple forming pockets in each annular row of staple forming pockets can be substantially equal for every annular row of staple forming pockets. The anvil assembly can include staple forming pockets wherein a length of each staple forming pocket of an inner annular row of staple forming pockets is relatively shorter than a length of each staple forming pocket of an outer annular row of staple forming pockets.

The anvil plate can define at least two annular rows of staple forming pockets, or at least three annular rows of staple forming pockets. In certain embodiments, the anvil plate defines an inner annular row of staple forming pockets, a middle annular row of staple forming pockets, and an outer annular row of staple forming pockets.

A length of each staple forming pocket of the middle annular row of staple forming pockets can be relatively longer than a length of each staple forming pocket of the inner annular row of staple forming pockets. A length of each staple forming pocket of the outer annular row of staple forming pockets can be relatively longer than a length of each staple forming pocket of the middle annular row of staple forming pockets.

In certain embodiments, a distance between adjacent staple forming pockets in the inner annular row of staple forming pockets is substantially equal to a distance between adjacent staple forming pockets in the middle annular row of staple forming pockets. A distance between adjacent staple forming pockets in the middle annular row of staple forming pockets can be substantially equal to a distance between adjacent staple forming pockets in the outer annular row of staple forming pockets.

In certain embodiments, the staple forming pockets of at least two adjacent annular rows of staple forming pockets are nested with one another. As such, the usage of a surface of the anvil is maximized for staple capture. Additionally, the nesting of the at least two adjacent annular rows of staple forming pockets helps to maintain uniform radial and longitudinal spacing of the staples for even pressure distribution on the tissue.

According to another aspect of the present disclosure, an end effector for use with a surgical stapler is provided. The end effector comprises anvil assembly including an anvil center rod having a proximal end and a distal end, the center rod defining a central longitudinal axis; and an anvil head secured to the distal end of the anvil center rod. The anvil head includes an anvil plate defining a tissue contact surface; and a plurality of staple forming pockets formed in the tissue contact surface of the anvil plate, wherein each of the plurality of staple pockets has a curved length. The end effector further includes a staple cartridge assembly defining a plurality of staple retaining slots corresponding to a number of staple forming pockets of the anvil assembly, the staple cartridge assembly comprising a plurality of surgical staples supported therein in a spaced relation to each other.

In certain embodiments, each of the plurality of staple retaining slots of the staple cartridge assembly has a curved length. Each staple forming pocket of the anvil assembly can a radius of curvature extending from the central longitudinal axis of the center rod. Each staple retaining slot of the staple cartridge assembly may have a radius of curvature extending from a central longitudinal axis of the surgical stapler.

The anvil assembly can be circular and define a plurality of annular rows of staple forming pockets, and the cartridge assembly can be circular and define a plurality of annular rows of staple retaining slots.

Each annular row of staple forming pockets of the anvil assembly can include an equal number of staple forming pockets. Each annular row of staple retaining slots of the staple cartridge assembly can include an equal number of staple retaining slots.

A distance between adjacent staple forming pockets in each annular row of staple forming pockets of the anvil assembly can be substantially equal for every annular row of staple forming pockets. A distance between adjacent staple retaining clots in each annular row of staple retaining slots of the staple cartridge assembly is substantially equal for every annular row of staple forming pockets.

A length of each staple forming pocket of an inner annular row of staple forming pockets of the anvil assembly can be relatively shorter than a length of each staple forming pocket of an outer annular row of staple forming pockets of the anvil assembly. A length of each staple retaining slot of an inner annular row of staple retaining slots of the staple cartridge assembly can be relatively shorter than a length of each staple retaining slot of a middle annular row of staple retaining slots of the staple cartridge assembly.

The anvil plate of the anvil assembly can define at least two annular rows of staple forming pockets, or at least three annular rows of staple forming pockets. The staple cartridge assembly can define at least two annular rows of staple retaining slots, or at least three annular rows of staple retaining slots.

The anvil plate of the anvil assembly can define an inner annular row of staple forming pocket, a middle annular row of staple forming pockets and an outer annular row of staple forming pockets. The staple cartridge assembly can define an inner annular row of staple retaining slots, a middle annular row of staple retaining slots and an outer annular row of staple retaining slots.

A length of each staple forming pocket of the middle annular row of staple forming pockets of the anvil assembly may be relatively longer than a length of each staple forming pocket of the inner annular row of staple forming pockets of the anvil assembly. A length of each staple forming pocket of the outer annular row of staple forming pockets of the anvil assembly may be relatively longer than a length of each staple forming pocket of the middle annular row of staple forming pockets of the anvil assembly.

A length of each staple retaining slot of the middle annular row of staple retaining slots of the staple cartridge assembly can be relatively longer than a length of each staple retaining slot of the inner annular row of staple retaining slots of the staple cartridge assembly. A length of each staple retaining slot of the outer annular row of staple retaining slots of the staple cartridge assembly can be relatively longer than a length of each staple retaining slot of the middle annular row of staple retaining slots of the staple cartridge assembly.

A distance between adjacent staple forming pockets in the inner annular row of staple forming pockets of the anvil assembly may be substantially equal to a distance between adjacent staple forming pockets in the middle annular row of staple forming pockets of the anvil assembly. A distance between adjacent staple forming pockets in the middle annular row of staple forming pockets of the anvil assembly may be substantially equal to a distance between adjacent staple forming pockets in the outer annular row of staple forming pockets of the anvil assembly.

A distance between adjacent staple retaining slots in the inner annular row of staple retaining slots of the staple cartridge assembly can be substantially equal to a distance between adjacent staple retaining slots in the middle annular row of staple retaining slots of the staple cartridge assembly. A distance between adjacent staple retaining slots in the middle annular row of staple retaining slots of the staple cartridge assembly can be substantially equal to a distance between adjacent staple retaining slots in the outer annular row of staple retaining slots of the staple cartridge assembly.

The staple forming pockets of at least two adjacent annular rows of staple forming pockets of the anvil assembly may be nested with one another. The staple cartridge can include surgical staples that have a curved backspan.

Each staple retaining slot of each annular row of staple retaining slots of the staple cartridge can be loaded with a surgical staple having a backspan with an appropriate length that corresponds to the length of the staple retaining slot. Each staple retaining slot of each annular row of staple retaining slots of the staple cartridge can be loaded with a surgical staple having a backspan with an appropriate length that corresponds to the length of the staple retaining slot.

A length of the backspan of the surgical staples loaded in each staple retaining slot of the middle annular row of staple retaining slots of the staple cartridge assembly can be relatively longer than a length of the backspan of the surgical staples loaded in each staple retaining slot of the inner annular row of staple retaining slots of the staple cartridge assembly. A length of the backspan of the surgical staples loaded in each staple retaining slot of the outer annular row of staple retaining slots of the staple cartridge assembly can be relatively longer than a length of the backspan of the surgical staples loaded in each staple retaining slot of the middle annular row of staple retaining slots of the staple cartridge assembly.

Each surgical staple can include a backspan and a leg depending from each opposed end of the backspan, wherein the legs define a plane, and wherein the backspan is arcuate and projects in a direction out of the plane defined by the legs of the surgical staple.

According to yet another aspect of the present disclosure, a surgical stapler is provided and comprises a handle assembly including a stationary handle, an approximation mechanism, and a firing trigger for firing a plurality of surgical fasteners; and an end effector supported on a distal end of the handle assembly. The end effector comprising an anvil assembly including an anvil center rod having a proximal end configured for selective connection to the approximation mechanism and a distal end, the center rod defining a central longitudinal axis; and an anvil head secured to the distal end of the anvil center rod. The anvil head includes an anvil plate defining a tissue contact surface; and a plurality of staple forming pockets formed in the tissue contact surface of the anvil plate, wherein each of the plurality of staple pockets has a curved length. The end effector further includes a staple cartridge assembly defining a plurality of staple retaining slots corresponding to a number of staple forming pockets of the anvil assembly, the staple cartridge assembly comprising a plurality of surgical staples supported therein in a spaced relation to each other.

Each of the plurality of staple retaining slots of the staple cartridge assembly may have a curved length.

Each staple forming pocket of the anvil assembly may have a radius of curvature extending from the central longitudinal axis of the center rod. Each staple retaining slot of the staple cartridge assembly may have a radius of curvature extending from a central longitudinal axis of the surgical stapler.

The anvil assembly may be circular and may define a plurality of annular rows of staple forming pockets, and the cartridge assembly may be circular and may define a plurality of annular rows of staple retaining slots.

Each annular row of staple forming pockets of the anvil assembly may include an equal number of staple forming pockets.

Each annular row of staple retaining slots of the staple cartridge assembly may include an equal number of staple retaining slots.

A distance between adjacent staple forming pockets in each annular row of staple forming pockets of the anvil assembly may be substantially equal for every annular row of staple forming pockets. A distance between adjacent staple retaining clots in each annular row of staple retaining slots of the staple cartridge assembly may be substantially equal for every annular row of staple forming pockets.

A length of each staple forming pocket of a inner annular row of staple forming pockets of the anvil assembly may be relatively shorter than a length of each staple forming pocket of a outer annular row of staple forming pockets of the anvil assembly. A length of each staple retaining slot of a inner annular row of staple retaining slots of the staple cartridge assembly may be relatively shorter than a length of each staple retaining slot of a outer annular row of staple retaining slots of the staple cartridge assembly.

The anvil plate of the anvil assembly may define at least two annular rows of staple forming pockets, or at least three annular rows of staple forming pockets. The staple cartridge assembly may define at least two annular rows of staple retaining slots, or at least three annular rows of staple retaining slots.

The anvil plate of the anvil assembly may define an inner annular row of staple forming pocket, a middle annular row of staple forming pockets and an outer annular row of staple forming pockets. The staple cartridge assembly may define an inner annular row of staple retaining slots, a middle annular row of staple retaining slots and an outer annular row of staple retaining slots.

A length of each staple forming pocket of the middle annular row of staple forming pockets of the anvil assembly may be relatively longer than a length of each staple forming pocket of the inner annular row of staple forming pockets of the anvil assembly. A length of each staple forming pocket of the outer annular row of staple forming pockets of the anvil assembly may be relatively longer than a length of each staple forming pocket of the middle annular row of staple forming pockets of the anvil assembly.

A length of each staple retaining slot of the middle annular row of staple retaining slots of the staple cartridge assembly may be relatively longer than a length of each staple retaining slot of the inner annular row of staple retaining slots of the staple cartridge assembly. A length of each staple retaining slot of the outer annular row of staple retaining slots of the staple cartridge assembly may be relatively longer than a length of each staple retaining slot of the middle annular row of staple retaining slots of the staple cartridge assembly.

A distance between adjacent staple forming pockets in the inner annular row of staple forming pockets of the anvil assembly may be substantially equal to a distance between adjacent staple forming pockets in the middle annular row of staple forming pockets of the anvil assembly. A distance between adjacent staple forming pockets in the middle annular row of staple forming pockets of the anvil assembly may be substantially equal to a distance between adjacent staple forming pockets in the outer annular row of staple forming pockets of the anvil assembly.

A distance between adjacent staple retaining slots in the inner annular row of staple retaining slots of the staple cartridge assembly may be substantially equal to a distance between adjacent staple retaining slots in the middle annular row of staple retaining slots of the staple cartridge assembly. A distance between adjacent staple retaining slots in the middle annular row of staple retaining slots of the staple cartridge assembly may be substantially equal to a distance between adjacent staple retaining slots in the outer annular row of staple retaining slots of the staple cartridge assembly.

The staple forming pockets of at least two adjacent annular rows of staple forming pockets of the anvil assembly may be nested with one another.

Each staple retaining slot of each annular row of staple retaining slots of the staple cartridge may be loaded with a surgical staple having a backspan with an appropriate length that corresponds to the length of the staple retaining slot.

Each staple retaining slot of each annular row of staple retaining slots of the staple cartridge may be loaded with a surgical staple having a backspan with an appropriate length that corresponds to the length of the staple retaining slot. A length of the backspan of the surgical staples loaded in each staple retaining slot of the middle annular row of staple retaining slots of the staple cartridge assembly may be relatively longer than a length of the backspan of the surgical staples loaded in each staple retaining slot of the inner annular row of staple retaining slots of the staple cartridge assembly. A length of the backspan of the surgical staples loaded in each staple retaining slot of the outer annular row of staple retaining slots of the staple cartridge assembly may be relatively longer than a length of the backspan of the surgical staples loaded in each staple retaining slot of the middle annular row of staple retaining slots of the staple cartridge assembly.

Each staple may have a backspan that is curved. Each surgical staple may include a backspan and a leg depending from each opposed end of the backspan, wherein the legs define a plane, and wherein the backspan is arcuate and projects in a direction out of the plane defined by the legs of the surgical staple.

DESCRIPTION OF THE DRAWINGS

Various embodiment of the presently disclosed circular surgical stapling device are disclosed herein with reference to the drawings, wherein.

DETAILED DESCRIPTION OF EMBODIMENTS

Figure 1:
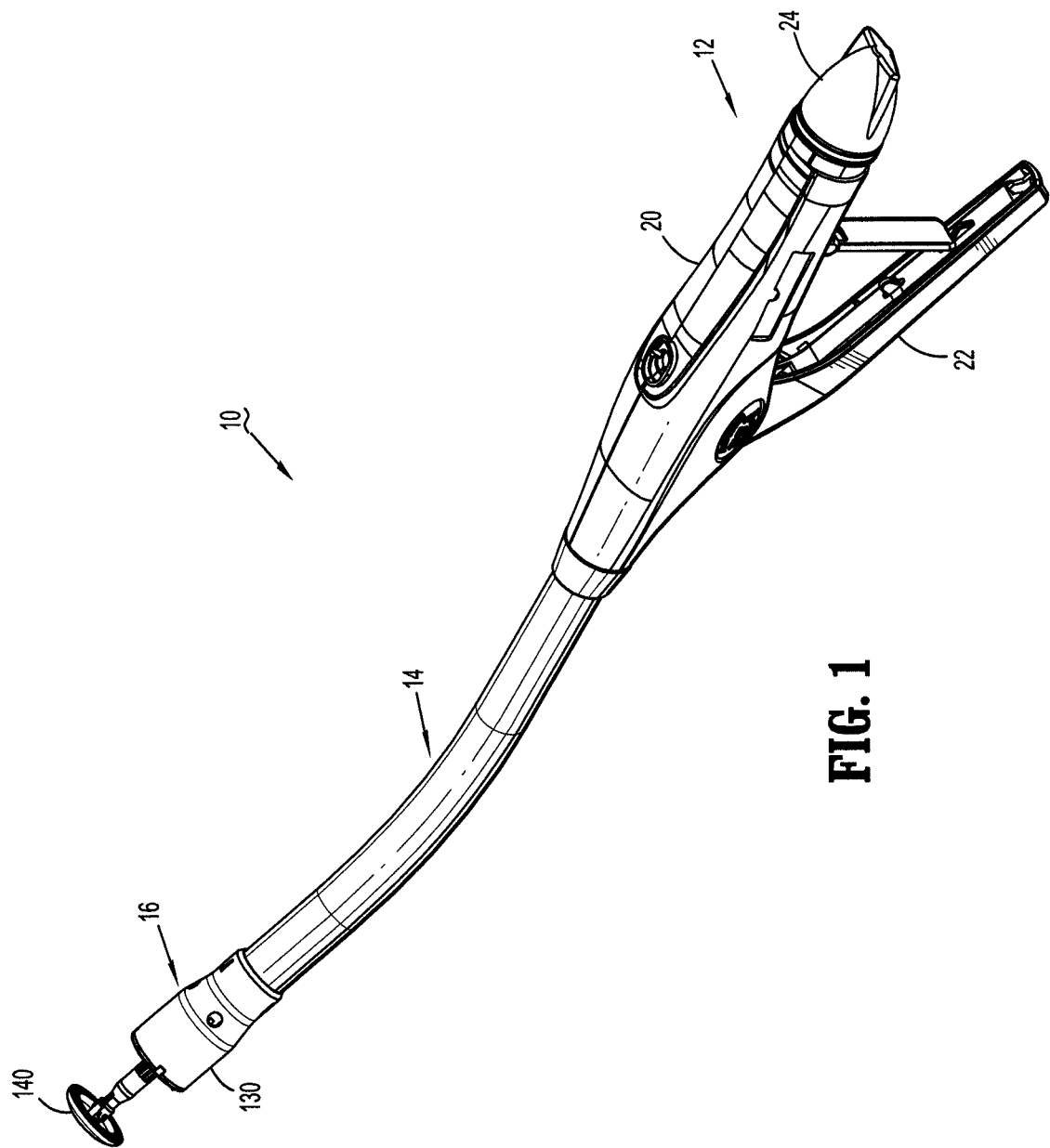
FIG. 1 is a perspective view of a circular surgical stapling device according to an embodiment of the present disclosure.

Various exemplary embodiments of the presently disclosed anvil assembly and cartridge assembly for a circular stapling device, will now be described in detail with reference to the drawings wherein similar reference characters identify similar or identical elements. In the drawings, and in the following description, the term "proximal" will refer to the end of the anvil assembly, cartridge assembly or circular stapling device, or component thereof, that is closest to the operator during proper use, while the term "distal" will refer to the end that is furthest from the operator, as is traditional and conventional in the art. In addition, the term "surgical fastener" should be understood to include any substantially rigid structure formed of a biocompatible material that is suitable for the intended purpose of joining together adjacent tissue portions, including but not being limited to surgical staples, clips, two-part fasteners and the like.

FIG. 1 illustrates a circular stapling device, referred to generally by the reference character 10. Briefly, surgical stapling device 10 includes a handle assembly 12, an elongated central body portion 14 extending from handle assembly 12, and a distal head portion 16 supported on or at a distal end of central body portion 14. The length and/or configuration of the central body portion 14 may be altered or varied to suit the requirements of the particular surgical procedure in which the surgical fastener applying apparatus may be employed. For example, the central body portion 14 may be either substantially straight, e.g., when intended for use in a procedure for the treatment of hemorrhoids, or alternatively, the central body portion may be curved. The central body portion may be flexible. The transverse dimensions of the body portion 14 and/or the head portion 16 may also be varied to suit a particular surgical procedure.

The handle assembly 12 includes a stationary handle 20, a firing trigger 22, and a rotatable approximation knob 24. The head portion 16 includes a shell assembly 130, and an anvil assembly 140. The shell assembly 130 is configured, dimensioned, and adapted to accommodate a plurality of surgical fasteners 150, an example of which can be seen in FIG. 1, that are used to attach adjacent portions of a patient's tissue. The staples or other fasteners can be contained in a cartridge or loading unit. The shell assembly 130 and the anvil assembly 140 of head portion 16 includes additional components, and performs additional functions, each of which is discussed in commonly assigned U.S. Pat. No. 7,234,624 to Gresham et al., entitled "Surgical Stapling Device for Performing Circular Anastomoses," the entire content of which is incorporated by reference herein.

Figure 2:
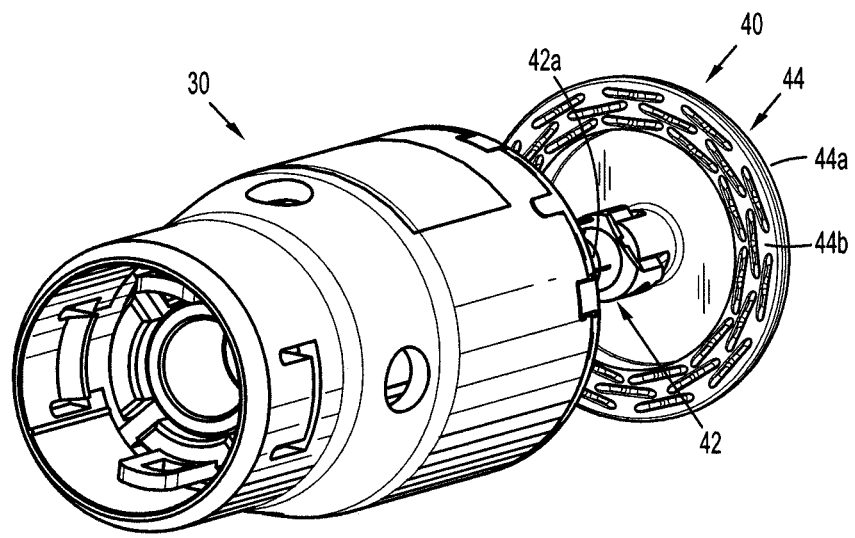
FIG. 2 is a rear perspective view of a prior art shell assembly and anvil assembly.
Figure 3:
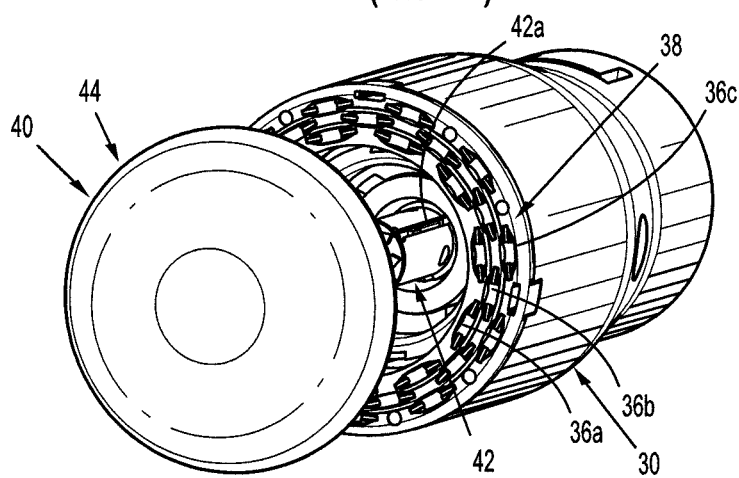
FIG. 3 is a front perspective view of the prior art anvil assembly and shell assembly of FIG. 2.
Figure 5:
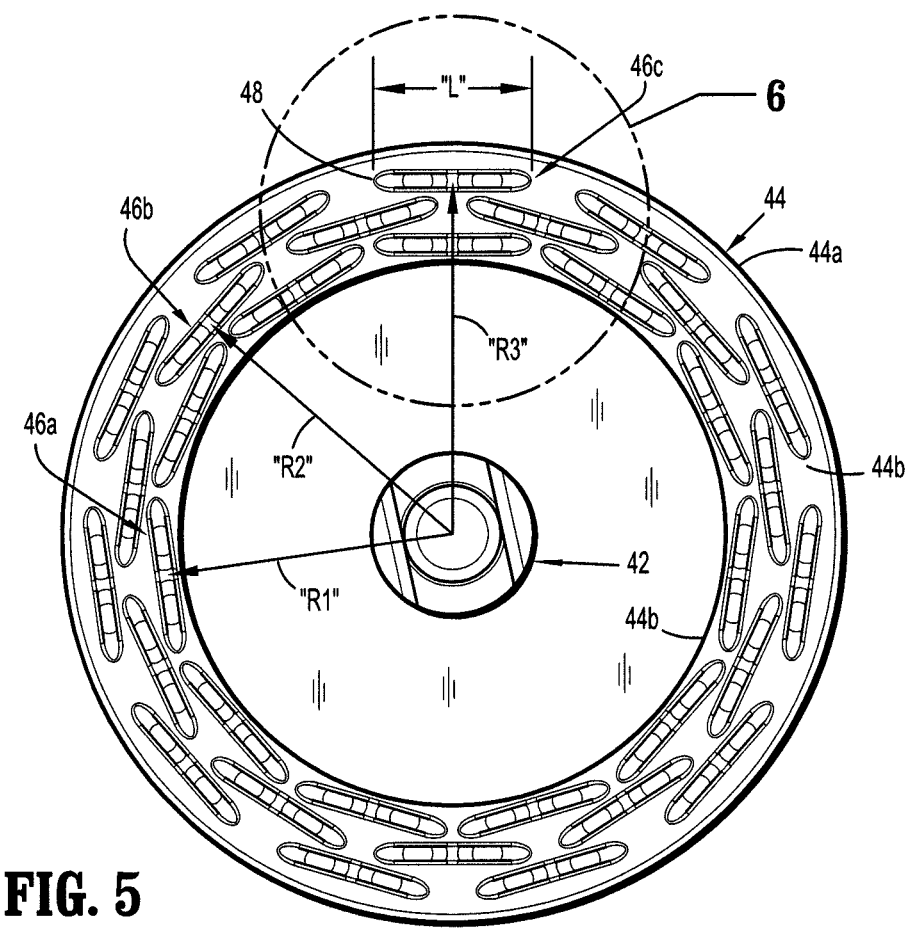
FIG. 5 is a plan view of a tissue contact surface of an anvil plate of the anvil assembly of FIGS. 2 and 3.
Figure 6:
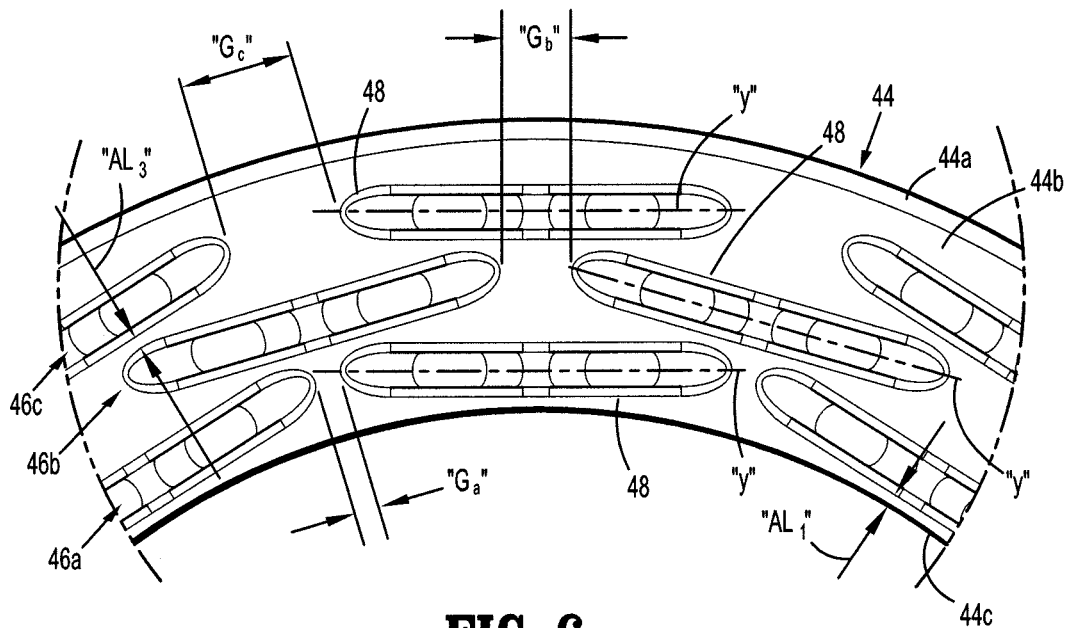
FIG. 6 is an enlarged view of the indicated area of detail of FIG. 5.

As seen in FIGS. 2, 3, 5 and 6, an anvil assembly according to the prior art is generally designated as 40. Anvil assembly 40 includes an anvil center rod assembly 42 and an anvil head assembly 44. As best seen in FIGS. 2 and 3, anvil center rod assembly 42 includes a center rod 42a and, as seen in FIGS. 2, 5 and 6, anvil head assembly 44 includes an anvil head 44a and an anvil plate 44b defining three concentric, annular rows 46a, 46b, 46c of respective staple forming pockets 48 for receiving and forming staples.

As seen in FIGS. 5 and 6, each staple forming pocket 48 defines a linear or straight longitudinal axis "Y". Also as seen in FIGS. 5 and 6, first or inner annular row 46a of staple forming pockets 48 is disposed along a radius "R1," second or middle annular row 46b of staple forming pockets 48 is disposed along a radius "R2" greater than radius "R1," and third or outer annular row 46c of staple forming pockets 48 is disposed along a radius "R3" greater than radius "R2." Each radius "R1", "R2" and "R3" being measured relative to a midpoint of each staple forming pocket 48.

As seen in FIGS. 5 and 6, since each staple forming pocket 48 defines a linear or straight longitudinal axis "Y," a radial distance from an anastomosis lip 44c of anvil head assembly 44 to each staple forming pocket 48 is not uniform or constant. In particular, a radial distance "$AL_1$" from anastomosis lip 44c to a mid-point of each staple forming pocket 48 is less than a radial distance "$AL_2$" from anastomosis lip 44c to either longitudinal end of each staple forming pocket 48.

Additionally, as seen in FIG. 6, since each staple forming pocket 48 defines a linear or straight longitudinal axis "Y," a radial distance "$AL_3$" between adjacent annular rows 46a, 46b, 46c of staple forming pockets 48 is also not uniform or constant. In particular, for example, a radial distance "$AL_3$" from either longitudinal end of each staple forming pocket 48 of a relatively radially inner annular row (e.g., 46a, 46b) of staple forming pockets 48 to a mid-point of each staple forming pocket 48 of a relatively radially outer annular row (e.g., 46b, 46c) of staple forming pockets 48 is less than a radial distance from a mid-point of each staple forming pocket 48 of the relatively radially outer annular row (e.g., 46b, 46c) of staple forming pockets 48 to either longitudinal end of each staple forming pocket 48 of the relatively radially inner annular row (e.g., 46c, 46b) of staple forming pockets 48.

Being that each annular row 46a, 46b and 46c includes an equal number of staple forming pockets 48 and being that each staple forming pocket 48 has an equal length "L", as seen in FIGS. 5 and 6, a distance between adjacent staple forming pockets 48, in each annular row 46a, 46b, 46c, increases as the radius of the annular row 46a, 46b, 46c increases. In particular, the first or inner annular row 46a of staple forming pockets 48 defines a first distance "Ga" between adjacent staple forming pockets 48 thereof. The second or middle annular row 46b of staple forming pockets 48 defines a second distance "Gb" between adjacent staple forming pockets 48 thereof that is greater than the first distance "Ga" between adjacent staple forming pockets 48 of first or inner annular row 46a. The third or outer annular row 46c of staple forming pockets 48 defines a third distance "Gc" between adjacent staple forming pockets 48 thereof that is greater than the second distance "Gb" between adjacent staple forming pockets 48 of second or middle annular row 46b.

Additionally, since each staple forming pocket 48 has a straight or linear shape, and since all the staple forming pockets 48 have a uniform or equal length "L", a the radii (R1, R2, R3) of adjacent annular rows 46a, 46b, 46c has to be selected so that the staple forming pockets 48 of one annular row 46a, 46b, 46c do not interfere with the staple forming pockets 48 of an adjacent annular row 46a, 46b, 46c.

As best seen in FIG. 3, a staple cartridge assembly according to the prior art is generally designated as 30. Staple cartridge assembly 30 includes a plurality of staple retaining slots 38 arranged in three concentric, annular rows 36a, 36b, 36c. Each staple retaining slot 38 is configured to retain a surgical staple therein. In order to properly cooperate with anvil assembly 40, cartridge assembly 30 includes an equal or corresponding number of staple retaining slots 38 as staple forming pockets 46 of anvil assembly 40 that are in juxtaposed axial alignment with each other when anvil assembly 40 is connected to circular stapling device 10.

Figure 4:
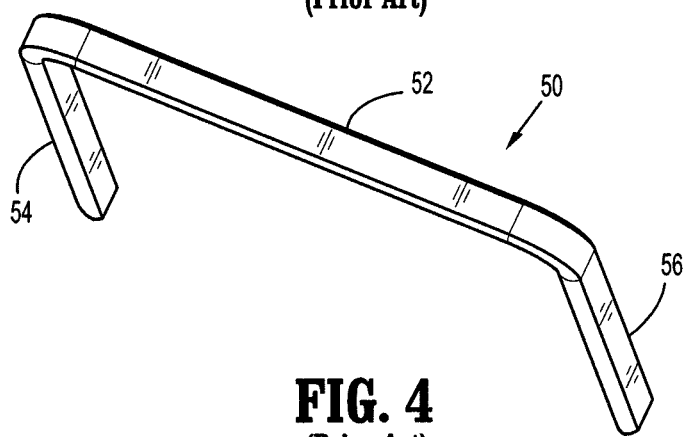
FIG. 4 is a perspective view of a prior art surgical staple.

As seen in FIG. 4, a surgical staple according to the prior art is generally designated as 50. Each surgical staple 50 includes a backspan 52 and a pair of legs 54, 56 depending from opposed ends of backspan 52. As seen in FIG. 4, backspan 52 of surgical staple 50 is substantially straight and linear, wherein backspan 52 lies within a plane defined by legs 54 and 56. Reference may be made to commonly owned and assigned U.S. Pat. Nos. 7,611,038 and 7,398,907, each entitled "Directionally Biased Staple and Anvil Assembly for Forming the Staple," the entire content of each of which being incorporated herein by reference, for a detailed discussion of the surgical staple 50.

Reference may additionally be made to commonly assigned U.S. Pat. No. 7,234,624 to Gresham et al., entitled "Surgical Stapling Device for Performing Circular Anastomoses," the entire content of which is incorporated by reference herein, for a detailed discussion and illustration of the operation and construction of circular stapling device 10. Generally, the anvil center rod is attached to an anvil retainer that is attached to a screw. Rotation of a knob retracts the screw and anvil retainer to approximate the anvil and cartridge assembly. A pivotable handle can be manipulated to advance a pusher link, advancing pushers and a knife, forming staples against the anvil and cutting tissue.

Reference may also be made to U.S. Patent Publication No. 2005/0187576, filed on Feb. 23, 2004, now U.S. Pat. No. 8,025,199, entitled "Surgical Cutting and Stapling Device," the entire content of which is incorporated by reference herein, for a detailed discussion and illustration of the operation and construction of a powered or electromechanical circular stapling device, that may be used with or may incorporate cartridge assemblies 130 and anvil assemblies 140 of the present disclosure, as discussed hereinbelow.

Turning now to FIGS. 1 and 5-16, a circular stapling device incorporating and/or for use with an end effector having a cartridge assembly 130, an anvil assembly 140 and a surgical staple 150, in accordance with the present disclosure, is shown and will be described. The handle assembly and elongated central body portion are substantially as described above. Alternatively, the end effector can be configured to be utilized with a handle assembly and body portion, shaft and/or adapter that are configured with a motor or for use with a motor or other energy source.

Figure 7:
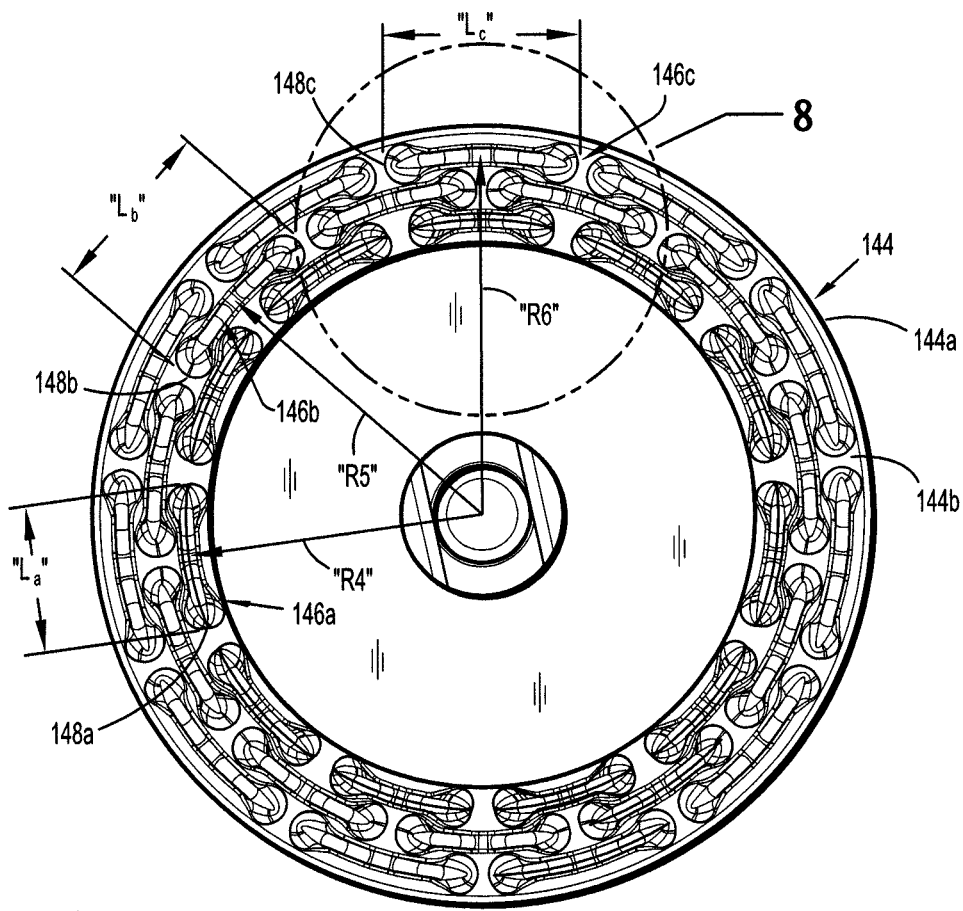
FIG. 7 is a plan view of an anvil plate according to an embodiment of the present disclosure for use in an anvil assembly of a circular stapling device.
Figure 8:
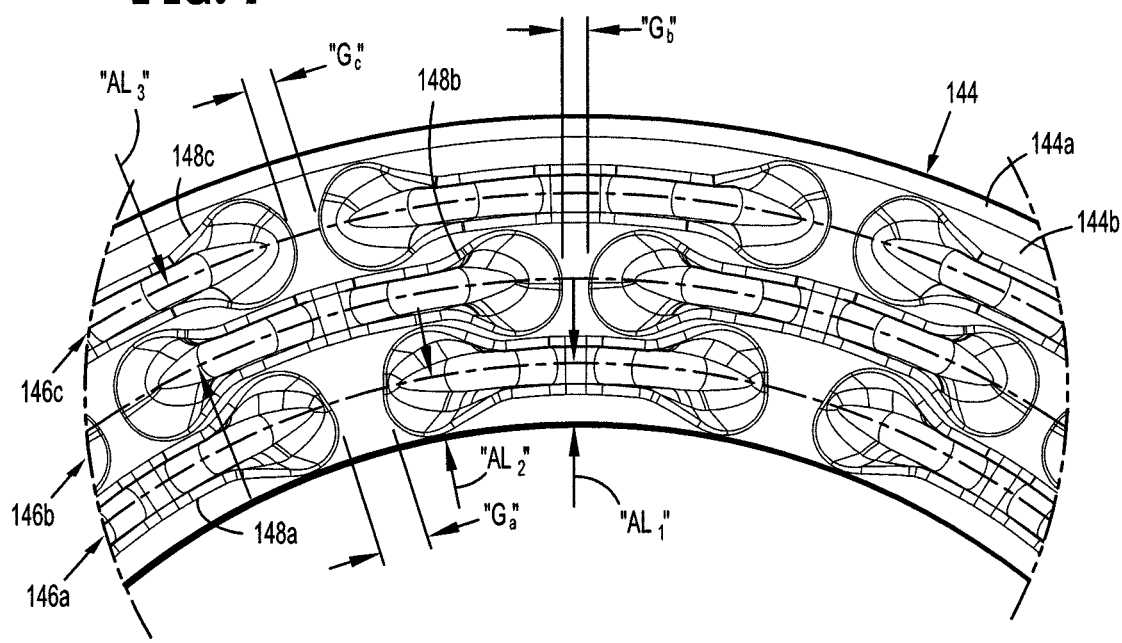
FIG. 8 is an enlarged view of the indicated area of detail of FIG. 7.

As seen in FIGS. 7 and 8, an anvil assembly, in accordance an embodiment of the present disclosure, is generally designated as 140. Anvil assembly 140 includes an anvil head 144a and an anvil plate 144b defining a plurality of concentric, annular rows 146a, 146b, 146c of respective staple forming pockets 148a, 148b, 148c for receiving and forming staples.

As seen in FIGS. 7 and 8, each staple forming pocket 148 defines an annular or arcuate longitudinal axis "Y1". The staple forming pockets have a curved, oblong shape. The curved length of each of the staple forming pockets follows the shape of the arcuate face of the anvil plate. The staple forming pockets have a crescent, biconcave shape to receive a staple having a curved backspan. Also as seen in FIGS. 7 and 8, first or inner annular row 146a of staple forming pockets 148 is disposed along a radius "R4," second or middle annular row 146b of staple forming pockets 148 is disposed along a radius "R5" greater than radius "R4," and third or outer annular row 146c of staple forming pockets 148 is disposed along a radius "R6" greater than radius "R5." Each radius "R4", "R5" and "R6" being measured relative to a midpoint of each staple forming pocket 148.

Since each staple forming pocket 148 defines an annular or arcuate longitudinal axis "Y1", a relative radial distance between radius "R4" and "R5" of respective first or inner annular row 146a and second or middle annular row 146b of anvil assembly 140 may be less than a relative radial distance between radius "R1" and "R2" of respective first or inner annular row 46a and second or middle annular row 46b of anvil assembly 40.

Additionally, a relative radial distance between radius "R5" and "R6" of respective second or middle annular row 146b and third or outer annular row 146c of anvil assembly 140 may be less than a relative radial distance between radius "R2" and "R3" of respective second or middle annular row 46b and third or outer annular row 46c of anvil assembly 40. As such, the annular rows 146a, 146b and 146c of staple forming pockets 148a, 148b, and 148c may be more closely packed with respect to one another.

With continued reference to FIGS. 7 and 8, each staple forming pocket 148 defines an annular or arcuate longitudinal axis "Ya, Yb and Yc" for respective annular rows 146a, 146b, 146c, and each annular row 146a, 146b and 146c includes an equal number of staple forming pockets 148. A length "La", "Lb" and "Lc" for respective staple forming pockets 148a, 148b, 148c in respective annular rows 146a, 146b, 146c may increase in a radially outward direction. In particular, the length "Lb" of staple forming pockets 148b in second or middle annular row 146b may be greater than the length "La" of staple forming pockets 148a in first or inner annular row 146a; and the length "Lc" of staple forming pockets 148c in third or outer annular row 146c may be greater than the length "Lb" of staple forming pockets 148b in second or middle annular row 146b.

In this manner, as seen in FIGS. 7 and 8, due to a difference in the lengths "La," "Lb," and "Lc" of respective staple forming pockets 148a, 148b and 148c, a distance between adjacent staple forming pockets 148a, 148b, 148c in each respective annular row 146a, 146b, 146c may be substantially equal. In particular, the first or inner annular row 146a of staple forming pockets 148a defines a first distance "Ga" between adjacent staple forming pockets 148a thereof. The second or middle annular row 146b of staple forming pockets 148b defines a second distance "Gb" between adjacent staple forming pockets 148b thereof that is substantially equal to the first distance "Ga" between adjacent staple forming pockets 148a of first or inner annular row 148a. The third or outer annular row 146c of staple forming pockets 148c defines a third distance "Gc" that is substantially equal to the first distance "Ga" between adjacent staple forming pockets 148a of first or inner annular row 148a and the second distance "Gb" between adjacent staple forming pockets 148b of second or middle annular row 148b.

Additionally, each staple forming pocket 148a, 148b, 148c may include a perimeterical profile or footprint having a central portion defined by a pair of parallel arcuate side walls interconnecting a pair of end portions defined by an enlarged bulbous or circular wall. Reference may be made to commonly owned and assigned U.S. Pat. Nos. 7,611,038 and 7,398,907, each entitled "Directionally Biased Staple and Anvil Assembly for Forming the Staple," the entire content of each of which being incorporated herein by reference, for a detailed discussion of the end portions of staple forming pockets 148a, 148b, 148c.

In this manner, as seen in FIGS. 7 and 8, staple forming pockets 148a, 148b and 148c of respective annular rows 146a, 146b and 146c may be nested with one another. The staple forming pockets can be formed utilizing stamping, coining, or other methods. Photolithography and/or microelectrolytic methods can be used. Microelectrolytic dissolution can be used to form the staple forming pockets in the anvil plate so that the staple forming pockets have a curved length.

As seen in FIGS. 7 and 8, since each staple forming pocket 148a, 148b, 148c of respective annular rows 146a, 146b and 146c defines an arcuate respective longitudinal axis "Ya, Yb, Yc," a radial distance from an anastomosis lip 144c of anvil head assembly 144 to each staple forming pocket 148a, 148b, 148c of respective annular rows 146a, 146b and 146c is substantially uniform or constant. In particular, a radial distance "$AL_1$" from anastomosis lip 144c to a mid-point of each staple forming pocket 148a, 148b, 148c of respective annular rows 146a, 146b and 146c is substantially equal to a radial distance "$AL_2$" from anastomosis lip 144c to either longitudinal end of each staple forming pocket 148a, 148b, 148c of respective annular rows 146a, 146b and 146c.

Additionally, as seen in FIG. 7, since each staple forming pocket 148a, 148b, 148c of respective annular rows 146a, 146b and 146c defines an arcuate respective longitudinal axis "Ya, Yb, Yc," a radial distance "$AL_3$" between adjacent annular rows 146a, 146b, 146c of staple forming pockets 148a, 148b, 148c is also substantially uniform or constant. In particular, for example, a radial distance "$AL_3$" from either longitudinal end of each staple forming pocket 148a, 148b of a relatively radially inner annular row (e.g., 146a, 146b) of staple forming pockets 148 to a mid-point of each staple forming pocket 148b, 148c of a relatively radially outer annular row (e.g., 146b, 146c) of staple forming pockets 148 is less than a radial distance from a mid-point of each staple forming pocket 148b, 148c of the relatively radially outer annular row (e.g., 146b, 146c) of staple forming pockets 148 to either longitudinal end of each staple forming pocket 148c, 148b of the relatively radially inner annular row (e.g., 146c, 146b) of staple forming pockets 148.

Figure 10:
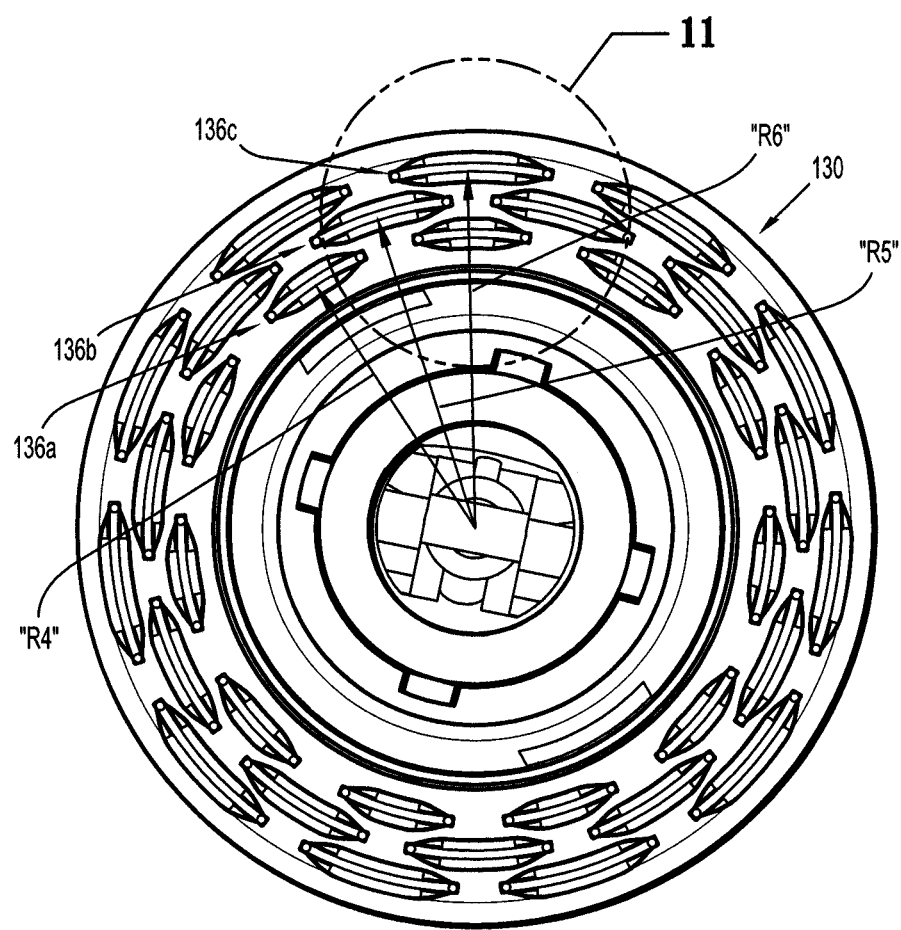
FIG. 10 is a plan view of a tissue contact surface of a cartridge assembly according to an embodiment of the present disclosure for use in a circular stapling device.
Figure 11:
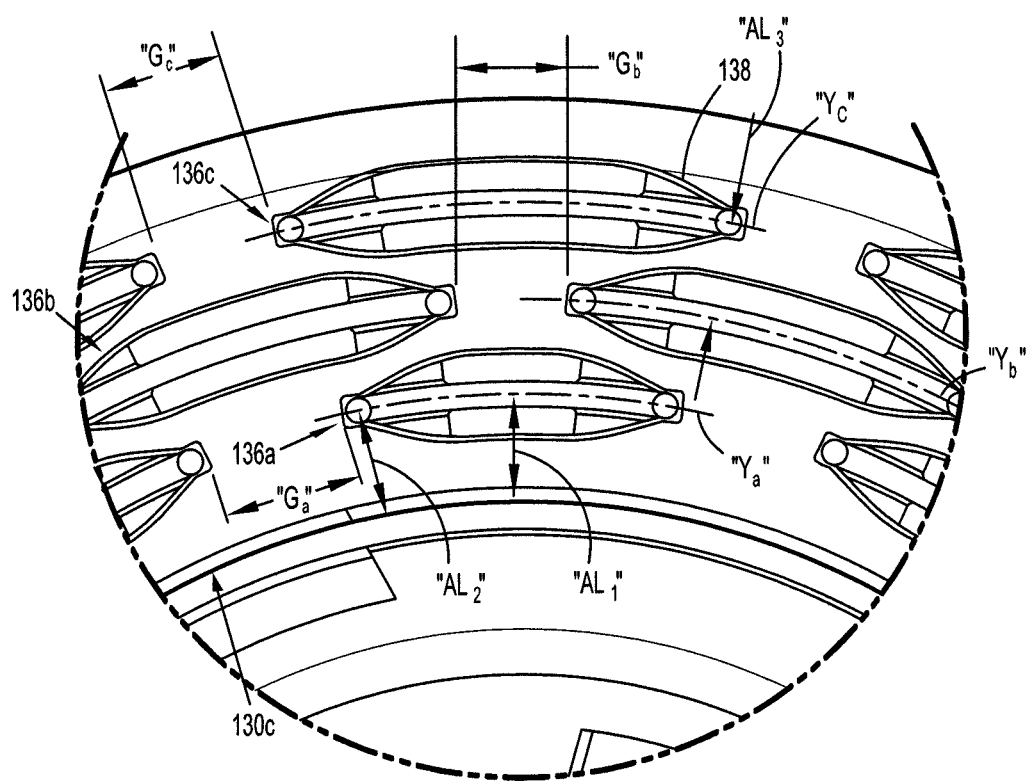
FIG. 11 is an enlarged view of the indicated area of detail of FIG. 10.

As best seen in FIGS. 10 and 11, a staple cartridge assembly, in accordance an embodiment of the present disclosure, is generally designated as 130. Staple cartridge assembly 130 includes a plurality of staple retaining slots 138 arranged in three concentric, annular rows 136a, 136b, 136c. Each staple retaining slot 138 is configured to retain a surgical staple therein. In order to properly cooperate with anvil assembly 140, cartridge assembly 130 includes an equal or corresponding number of staple retaining slots 138 as staple forming pockets 148 of anvil assembly 140 that are in juxtaposed axial alignment with each other when anvil assembly 140 is connected to circular stapling device 10.

As seen in FIGS. 10 and 11, each staple retaining slot 138 defines an annular or arcuate longitudinal axis "Ya, Yb and Yc" for respective annular rows 136a, 136b, 136c. The staple retaining slots have a curved, oblong shape. The curved length of each of the staple retaining slots follows the shape of the arcuate face of the cartridge assembly. The staple retaining slots have a crescent, biconcave shape to receive a staple having a curved backspan. Arcuate longitudinal axes "Ya, Yb and Yc" of staple retaining slots 138 for respective annular rows 136a, 136b, 136c is substantially similar to or has a substantially similar radius of curvature as arcuate longitudinal axes "Ya, Yb and Yc" of staple forming pockets 148 for respective annular rows 146a, 146b, 146c. Also as seen in FIGS. 10 and 11, first or inner annular row 136a of staple retaining slots 138 has a radius "R4," second or middle annular row 136b of staple retaining slots 138 has a radius "R5" greater than radius "R4," and third or outer annular row 136c of staple retaining slots 138 has a radius "R6" greater than radius "R5." Each radius "R4", "R5" and "R6" being measured relative to a midpoint of each staple retaining slot 138. Additionally, the radius for each staple retaining slot 138a, 138b, 138c for each annular row 136a, 136b, 136c is substantially constant or uniform along its entire length.

With continued reference to FIGS. 10 and 11, each staple retaining slot 138a, 138b, 138c defines respective annular or arcuate longitudinal axis "Ya, Yb and Yc", and annular row 136a, 136b and 136c includes an equal number of staple retaining slots 138. A length "La", "Lb" and "Lc" for respective staple retaining slots 138a, 138b, 138c in respective annular rows 136a, 136b, 136c may increase in a radially outward direction. In particular, the length "Lb" of staple retaining slots 138b in second or middle annular row 136b may be greater than the length "La" of staple retaining slots 138a in first or inner annular row 136a; and the length "Lc" of staple retaining slots 138c in third or outer annular row 136c may be greater than the length "Lb" of staple retaining slots 138b in second or middle annular row 136b. In other words, each staple retaining slot 138a, 138b, 138c in each respective annular row 136a, 136b, 136c has a length that substantially corresponds to or relates to the lengths "La," "Lb," and "Lc" of respective staple forming pockets 148a, 148b and 148c in each respective annular row 146a, 146b, 146c.

In this manner, as seen in FIGS. 10 and 11, due to a difference in the lengths "La," "Lb," and "Lc" of respective staple retaining slots 138a, 138b and 138c, a distance between adjacent staple retaining slots 138a, 138b and 138c in each respective annular row 136a, 136b, 136c may be substantially equal. In particular, the first or inner annular row 136a of staple retaining slots 138a defines a first distance "Ga" between adjacent staple retaining slots 138a, the second or middle annular row 136b of staple retaining slots 138b defines a second distance "Gb" that is substantially equal to the first distance "Ga," and the third or outer annular row 136c of staple retaining slots 138c defines a third distance "Gc" that is substantially equal to the first distance "Ga" between adjacent staple retaining slots 138a and the second distance "Gb" between adjacent staple retaining slots 138b.

As seen in FIGS. 10 and 11, since each staple retaining slot 138a, 138b, 138c of respective annular rows 136a, 136b and 136c defines an arcuate respective longitudinal axis "Ya, Yb, Yc," a radial distance from an anastomosis lip 130c of cartridge assembly 140 to each staple retaining slot 138a, 138b, 138c of respective annular rows 136a, 136b and 136c is substantially uniform or constant. In particular, a radial distance "AL$_1$" from anastomosis lip 130c to a mid-point of each staple retaining slot 138a, 138b, 138c of respective annular rows 136a, 136b and 136c is substantially equal to a radial distance "AL$_2$" from anastomosis lip 130c to either longitudinal end of each staple retaining slot 138a, 138b, 138c of respective annular rows 136a, 136b and 136c.

Additionally, as seen in FIG. 11, since each staple retaining slot 138a, 138b, 138c of respective annular rows 136a, 136b and 136c defines an arcuate respective longitudinal axis "Ya, Yb, Yc," a radial distance "AL$_3$" between adjacent annular rows 136a, 136b, 136c of staple retaining slots 138a, 138b, 138c is also substantially uniform or constant. In particular, for example, a radial distance "AL$_3$" from either longitudinal end of each staple retaining slot 138a, 138b of a relatively radially inner annular row (e.g., 136a, 136b) of staple retaining slots 138 to a mid-point of each staple retaining slot 138b, 138c of a relatively radially outer annular row (e.g., 136b, 136c) of staple retaining slots 138 is less than a radial distance from a mid-point of each staple retaining slot 138b, 138c of the relatively radially outer annular row (e.g., 136b, 136c) of staple retaining slots 138 to either longitudinal end of each staple retaining slot 138c, 138b of the relatively radially inner annular row (e.g., 136c, 136b) of staple retaining slots 138.

Figure 9:
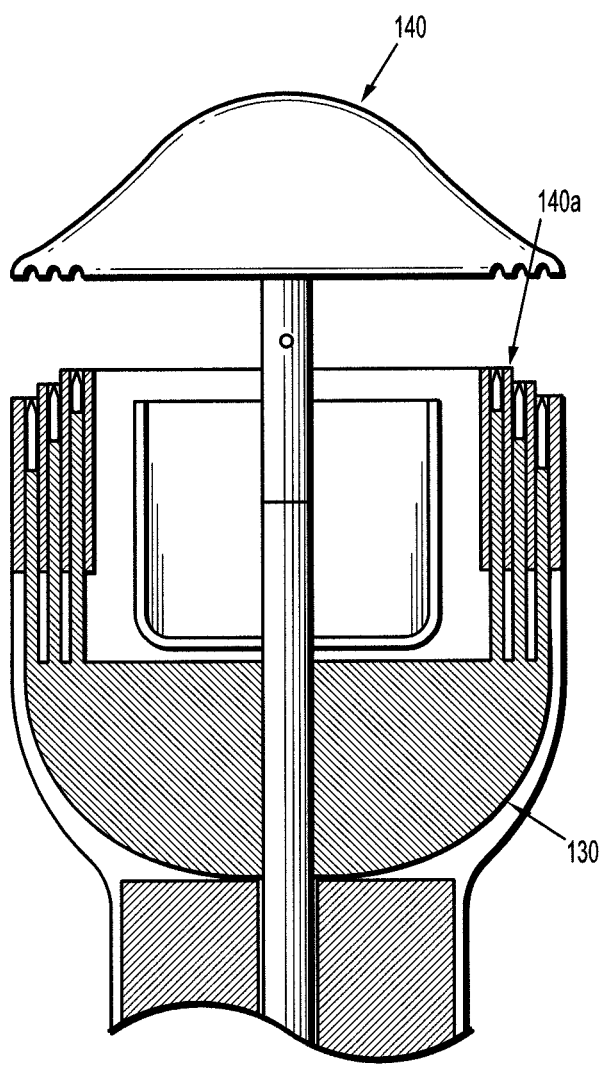
FIG. 9 is a schematic, longitudinal cross-sectional view of an anvil assembly and shell assembly according to another embodiment of the present disclosure.

Turning momentarily to FIG. 9, staple cartridge assembly, 130 may have a stepped tissue contacting surface 140a substantially similar to any of the tissue contacting surfaces shown and described in U.S. Pat. No. 7,398,908, entitled "Surgical Stapling Instruments Including a Cartridge having Multiple Staple Sizes," the entire content of which is incorporated herein by reference.

Figure 12:
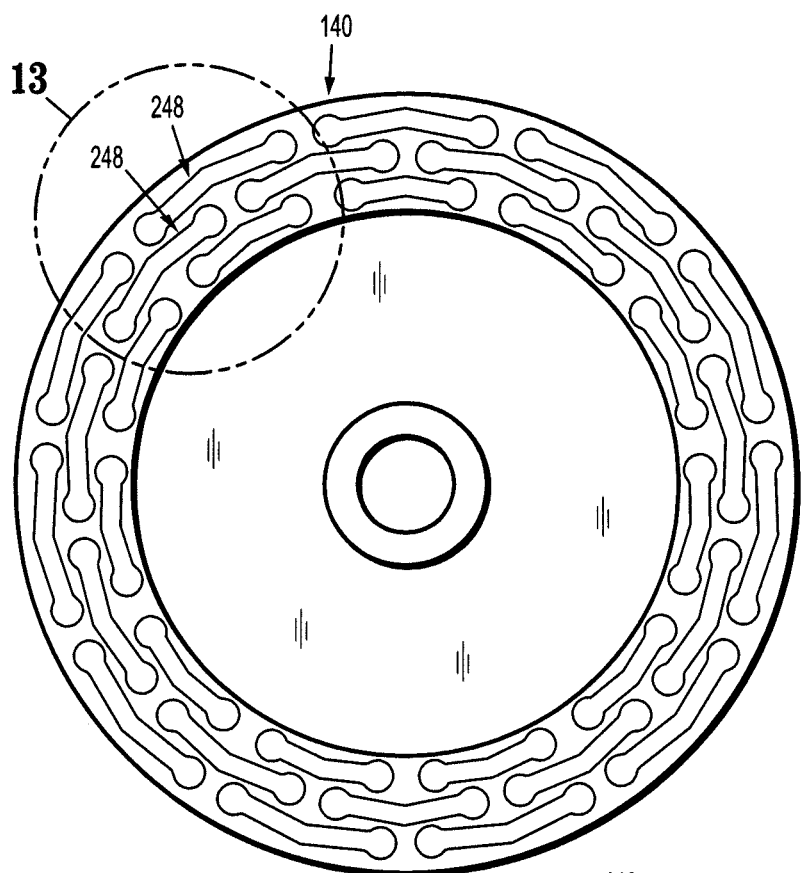
FIG. 12 is a plan view of a tissue contact surface of a cartridge assembly according to another embodiment of the present disclosure for use in a circular stapling device.
Figure 13:
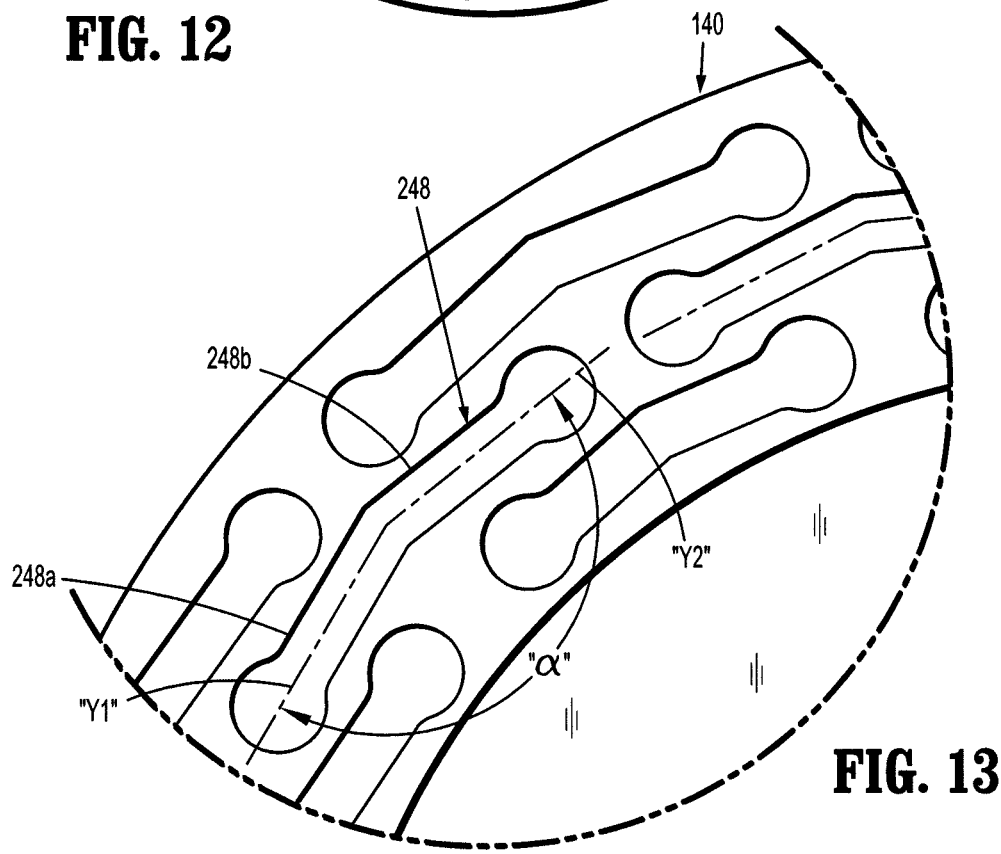
FIG. 13 is an enlarged view of the indicated area of detail of FIG. 12.

Turning now to FIGS. 12 and 13, staple forming pockets 248 for an anvil assembly 140, in accordance with another embodiment of the present disclosure are schematically shown and will be described. As seen in FIGS. 12 and 13, each staple forming pocket 248 defines a bent or non-linear longitudinal axis in order to approximate a curved or arcuate longitudinal axis. In particular, as seen in FIG. 13, each staple forming pocket 248 includes at least a first segment 248a defining a first linear longitudinal axis "Y1" and a second segment 248b defining a second linear longitudinal axis "Y2", wherein the first segment 248a and the second segment 248b are angled with respect to one another by an angle "α."

While FIGS. 12 and 13 have been described with relation to staple forming pockets for an anvil assembly 140, it is contemplated and within the scope of the present disclosure apply substantially equally to staple retaining slots for a staple cartridge assembly.

Figure 14:
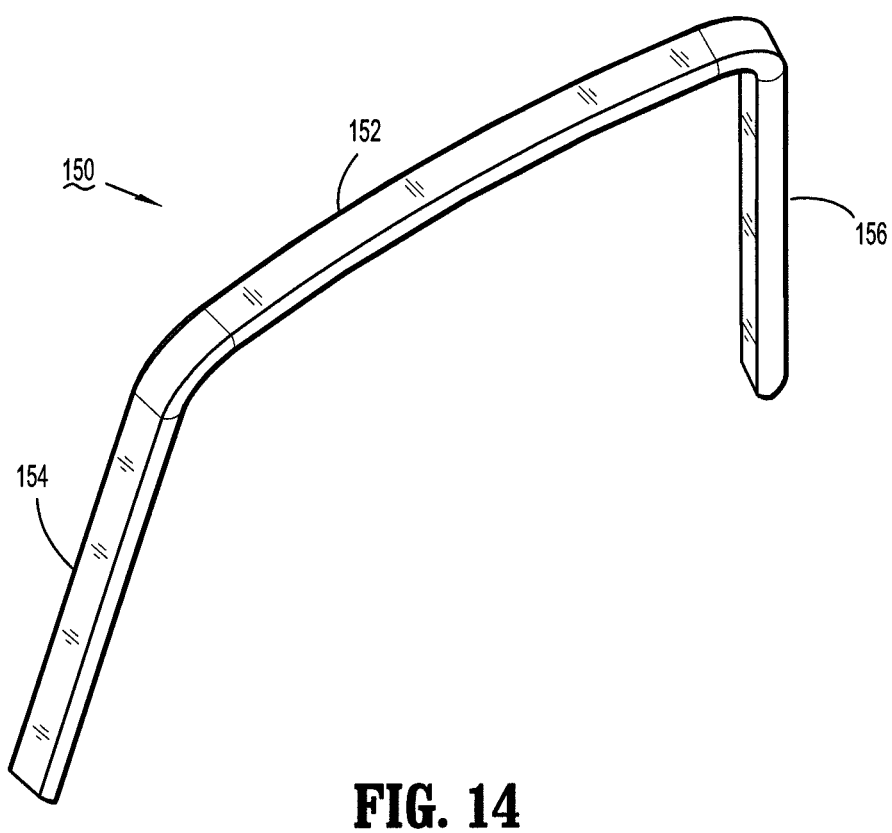
FIG. 14 is a perspective view of a surgical staple in accordance with an embodiment of the present disclosure for use in a circular stapling device.
Figure 15:
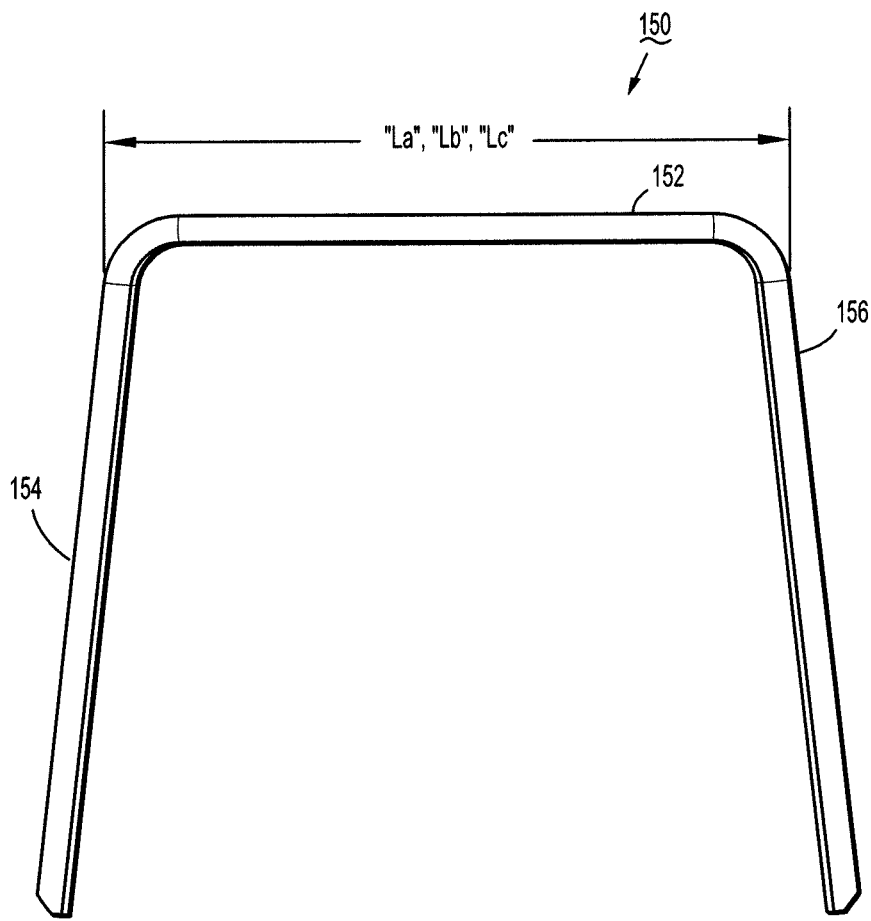
FIG. 15 is an elevational view of the surgical staple of FIG. 14.
Figure 16:
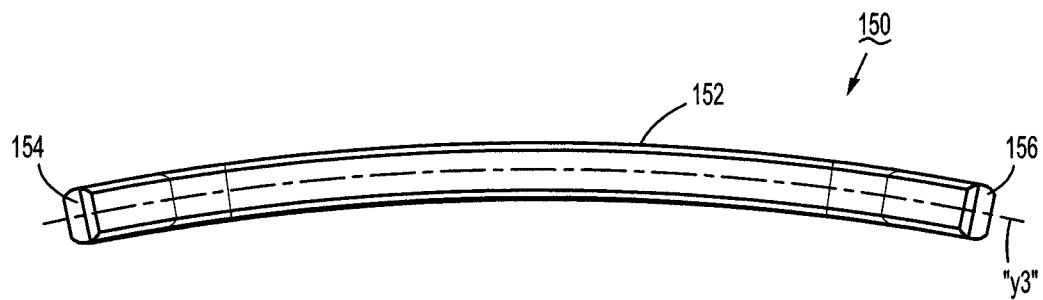
FIG. 16 is a top, plan view of the surgical staple of FIGS. 14 and 15.

As seen in FIGS. 14-16, a surgical staple, in accordance with embodiments of the present disclosure, is generally designated as 150. Each surgical staple 150 includes a backspan 152 and a pair of legs 154, 156 depending from opposed ends of backspan 152. As seen in FIGS. 14 and 16, backspan 152 of surgical staple 150 is curved and defines an arcuate longitudinal axis "Y3," wherein backspan 152 extends out of a plane defined by legs 154 and 156. Arcuate longitudinal axis "Y3" of backspan 152 of surgical staples 150 is substantially similar to or has a substantially similar radius of curvature as arcuate longitudinal axis "Ya, Yb and Yc" of respective staple forming pockets 148a, 148b, 148c and/or arcuate longitudinal axis "Ya, Yb, Yc" of staple retaining slots 138a, 138b, 138c.

Additionally, in accordance with the present disclosure, depending on which annular row 136a, 136b, 136c of staple retaining slot 138a, 138b, 138c that surgical staple 150 is loaded, surgical staple 150 will have a backspan 152 that has a length "La," "Lb" or "Lc" that corresponds to the length "La", "Lb" and "Lc" of respective staple retaining slots 138a, 138b, 138c. In particular, the surgical staples 150 loaded in first or inner annular row 136a of staple retaining slots 138a will have a backspan 152 with a length "La," the surgical staples 150 loaded in second or middle annular row 136b of staple retaining slots 138b will have a backspan 152 with a length "Lb," and the surgical staples 150 loaded in third or outer annular row 136c of staple retaining slots 138c will have a backspan 152 with a length "Lc." It is contemplated that as a length "La", "Lb" and "Lc" of backspan 152 of surgical staple 150 increases a corresponding length of legs 154 and 156 of surgical staple 150 decreases such that an overall length of material used to form surgical staples 150 loaded in respective annular rows 136a, 136b, 136c of staple retaining slots 138a, 138b, 138c remains substantially constant.

Moreover, as can be appreciated, in accordance with the present disclosure, the surgical staples 150 loaded in first or inner annular row 136a of staple retaining slots 138a will have a backspan 152 with a radius of curvature "R4," the surgical staples 150 loaded in second or middle annular row 136b of staple retaining slots 138b will have a backspan 152 with a radius of curvature "R5," and the surgical staples 150 loaded in third or outer annular row 136c of staple retaining slots 138c will have a backspan 152 with a radius of curvature "R6." The pusher member (or members) for driving the staples will have individual pusher plates that are curved to correspond to the shape of the backspan of the staples.

The staple forming pockets and staple retention slots discussed above have an inner row of pockets (or slots) that are spaced the same distance as an adjacent row of pockets (or slots) disposed outwardly of the inner row. As the spacing of the pockets (or slots) in the outwardly disposed row has been decreased as compared to the device discussed above in connection to FIGS. 2 through 4, a potential leak path is significantly smaller.

For the surgical stapler, end effector, and/or anvil assembly discussed above, two annular rows of surgical staples, two annular rows of staple retention slots and two annular rows of staple forming pockets may be used. The annular rows can be circular, ovoid, semi-circular, or in the shape of an arc. Additionally, a longitudinal axis of each staple retention slot and staple forming pocket may be angled or bent in order to approximate an arc. The rows of staple retention slots and rows of staple forming pockets with curved lengths can be used in surgical staplers and end effectors that have linear jaws or jaws of other shapes.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

What is claimed:

1. A circular anvil assembly, comprising:
   a center rod including:
      a proximal end portion configured to connect to an approximation mechanism; and
      a distal end portion; and
   an anvil head attached to the distal end portion of the center rod and having a tissue contacting surface, the tissue contacting surface defining a first circular row of staple forming pockets, the anvil head defining:
      a first radial distance between a curved, inner peripheral surface of the tissue contacting surface and a mid-point of a first staple forming pocket of the first circular row of staple forming pockets; and
      a second radial distance between the curved, inner peripheral surface of the tissue contacting surface and a first longitudinal end of the first staple forming pocket, wherein the first and second radial distances are equal to one another.

2. The circular anvil assembly according to claim 1, wherein the anvil head defines a third radial distance between the curved, inner peripheral surface of the tissue contacting surface and a second longitudinal end of the first staple forming pocket, wherein the first, second, and third radial distances are equal to one another.

3. The circular anvil assembly according to claim 1, wherein the first circular row of staple forming pockets defines an arcuate longitudinal axis, the mid-point of the first staple forming pocket being disposed on the arcuate longitudinal axis.

4. The circular anvil assembly according to claim 3, wherein an entirety of the first staple forming pocket is coaxial with the arcuate longitudinal axis.

5. The circular anvil assembly according to claim 1, wherein the tissue contacting surface further defines a second circular row of staple forming pockets.

6. The circular anvil assembly according to claim 5, wherein the first circular row of staple forming pockets is disposed closer to the curved, inner peripheral surface of the tissue contacting surface than is the second circular row of staple forming pockets.

7. The circular anvil assembly according to claim 6, wherein the second circular row of staple forming pockets is nested with the first circular row of staple forming pockets.

8. The circular anvil assembly according to claim 5, wherein each staple forming pocket of the second circular row of staple forming pockets is longer than each staple forming pocket of the first circular row of staple forming pockets.

9. The circular anvil assembly according to claim 5, wherein the mid-point of the first staple forming pocket is radially aligned with a point between adjacent longitudinal ends of adjacent staple forming pockets of the second circular row of staple forming pockets.

10. A staple cartridge assembly, comprising:
    a staple cartridge; and
    a tissue contacting surface supported on the staple cartridge and defining a first circular row of staple retaining slots, the staple cartridge defining:
       a first radial distance between a curved, inner peripheral surface of the tissue contacting surface and a mid-point of a first staple retaining slot of the first circular row of staple retaining slots; and
       a second radial distance between the curved, inner peripheral surface of the tissue contacting surface and a first longitudinal end of the first staple retaining slot, wherein the first and second radial distances are equal to one another.

11. The staple cartridge assembly according to claim 10, wherein the staple cartridge defines a third radial distance between the curved, inner peripheral surface of the tissue contacting surface and a second longitudinal end of the first staple retaining slot, wherein the first, second, and third radial distances are equal to one another.

12. The staple cartridge assembly according to claim 10, wherein the first circular row of staple retaining slots defines an arcuate longitudinal axis, the mid-point and opposing first and second longitudinal ends of the first staple retaining slot being disposed on the arcuate longitudinal axis.

13. The staple cartridge assembly according to claim 12, wherein an entirety of the first staple retaining slot is coaxial with the arcuate longitudinal axis.

14. The staple cartridge assembly according to claim 10, wherein the tissue contacting surface further defines a second circular row of staple retaining slots.

15. The staple cartridge assembly according to claim 14, wherein the first circular row of staple retaining slots is disposed closer to the curved, inner peripheral surface of the tissue contacting surface than is the second circular row of staple retaining slots.

16. The staple cartridge assembly according to claim 15, wherein the second circular row of staple retaining slots is nested with the first circular row of staple retaining slots.

17. The staple cartridge assembly according to claim 14, wherein each staple retaining slot of the second circular row of staple retaining slots is longer than each staple retaining slot of the first circular row of staple retaining slots.

18. The staple cartridge assembly according to claim 14, wherein the mid-point of the first staple retaining slot is radially aligned with a point between adjacent longitudinal ends of adjacent staple retaining slots of the second circular row of staple retaining slots.

19. The circular anvil assembly according to claim 1, wherein the first staple forming pocket curves from the mid-point to the first longitudinal end thereof.

20. The staple cartridge assembly according to claim 10, wherein the first staple retaining slot curves along a length thereof.

* * * * *